United States Patent
Moon et al.

(10) Patent No.: US 12,318,429 B2
(45) Date of Patent: Jun. 3, 2025

(54) PEPTIDE FOR PREVENTING OR TREATING HAIR LOSS, AND USE THEREOF

(71) Applicant: DAEGU GYEONGBUK INSTITUTE OF SCIENCE AND TECHNOLOGY, Daegu (KR)

(72) Inventors: Cheil Moon, Daegu (KR); So Yeon Kim, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 432 days.

(21) Appl. No.: 17/906,741

(22) PCT Filed: Mar. 26, 2021

(86) PCT No.: PCT/KR2021/003780
§ 371 (c)(1),
(2) Date: Sep. 19, 2022

(87) PCT Pub. No.: WO2021/206335
PCT Pub. Date: Oct. 14, 2021

(65) Prior Publication Data
US 2023/0144955 A1 May 11, 2023

(30) Foreign Application Priority Data
Apr. 6, 2020 (KR) .......... 10-2020-0041539

(51) Int. Cl.
| | | |
|---|---|---|
| A61K 38/18 | (2006.01) | |
| A61P 17/14 | (2006.01) | |
| A61Q 5/00 | (2006.01) | |
| A61Q 7/00 | (2006.01) | |
| C07K 14/505 | (2006.01) | |

(52) U.S. Cl.
CPC .......... *A61K 38/1816* (2013.01); *A61P 17/14* (2018.01); *A61Q 5/00* (2013.01); *A61Q 7/00* (2013.01); *C07K 14/505* (2013.01)

(58) Field of Classification Search
None
See application file for complete search history.

(56) References Cited

U.S. PATENT DOCUMENTS

| | | |
|---|---|---|
| 2007/0161552 A1 | 7/2007 | Bahlmann et al. |
| 2017/0232066 A1* | 8/2017 | Cerami .................. A61P 39/00 514/7.7 |

FOREIGN PATENT DOCUMENTS

| | | |
|---|---|---|
| CN | 103501796 | 1/2014 |
| CN | 103957924 | 7/2014 |
| CN | 109908329 | 6/2019 |
| KR | 10-2010-0080112 | 7/2010 |
| KR | 10-2013-0032788 | 4/2013 |
| KR | 10-2020-0023991 | 3/2020 |
| WO | 2005-116053 | 12/2005 |
| WO | 2010077093 | 7/2010 |

OTHER PUBLICATIONS

Kang et al. Erythropoietin promotes hair shaft growth in cultured human hair follicles and modulates hair growth in mice. Journal of Dermatological Science 59:86-90; (2010). (Year: 2010).*
Wayne Whitwam et al., "Alopecia in Three Women of Southeast Asian Descent With Chronic Renal Failure: Possible Association With Erythropoietin Use", American Journal of Kidney Diseases, vol. 37, No. 1 (Jan. 2001): E9, total 1 page, English Abstract Only.

* cited by examiner

*Primary Examiner* — Elizabeth C. Kemmerer
*Assistant Examiner* — Regina M DeBerry
(74) *Attorney, Agent, or Firm* — LEX IP MEISTER, PLLC

(57) ABSTRACT

A peptide according to one aspect of the present invention, and a pharmaceutical composition and a skin external preparation containing same promote the growth of individual hair follicle cells and increase the amount of hair growth-related cytokines, thus having a hair tonic, hair growth, or hair growth-promoting effect, and consequently, the effect of effectively treating, ameliorating, or preventing alopecia.

13 Claims, 6 Drawing Sheets
Specification includes a Sequence Listing.

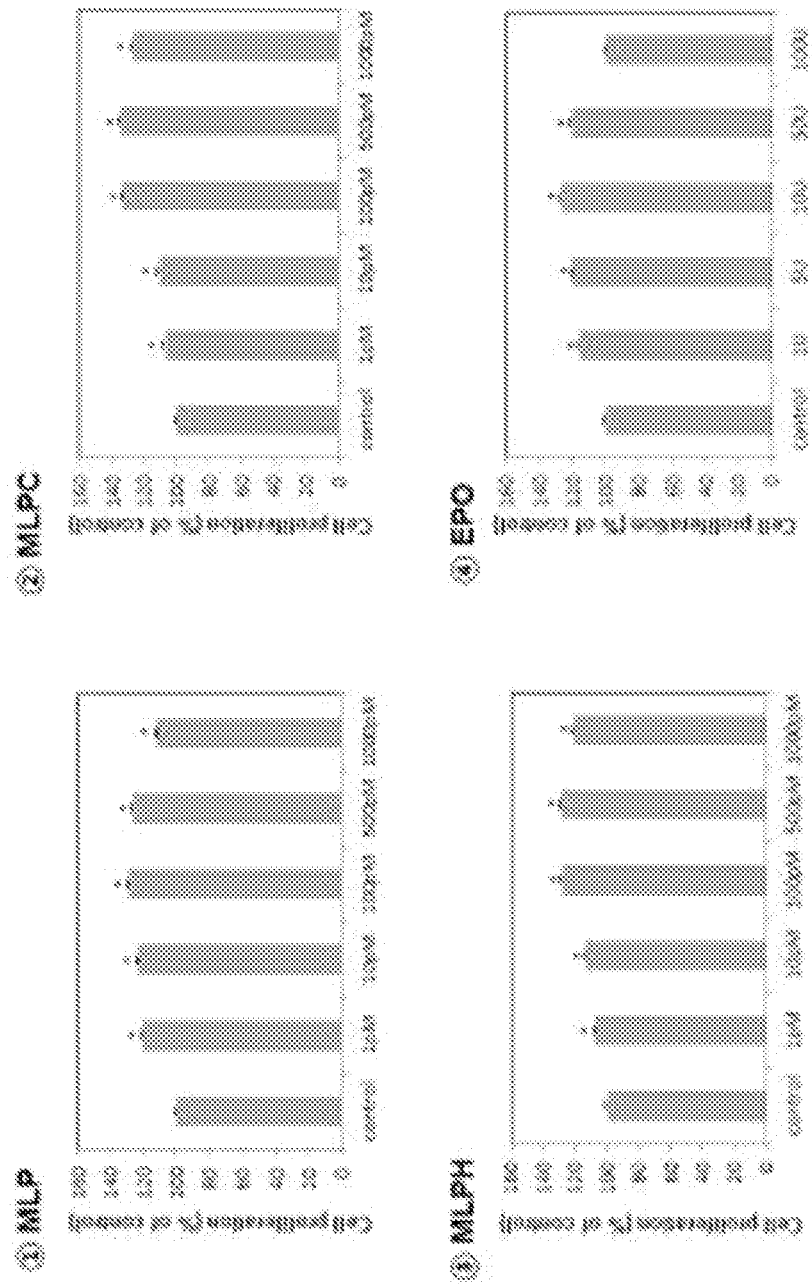
[FIG. 1]

[FIG. 2]
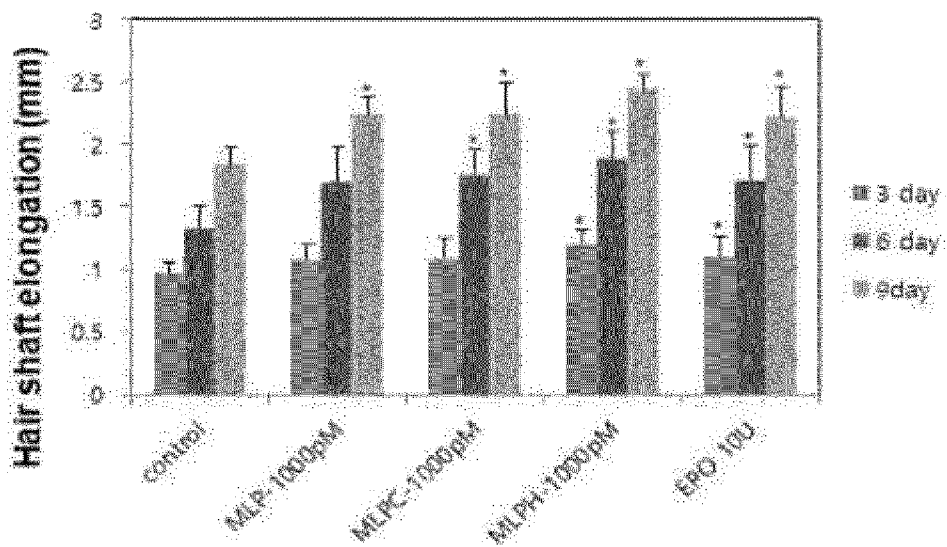
[FIG. 3]
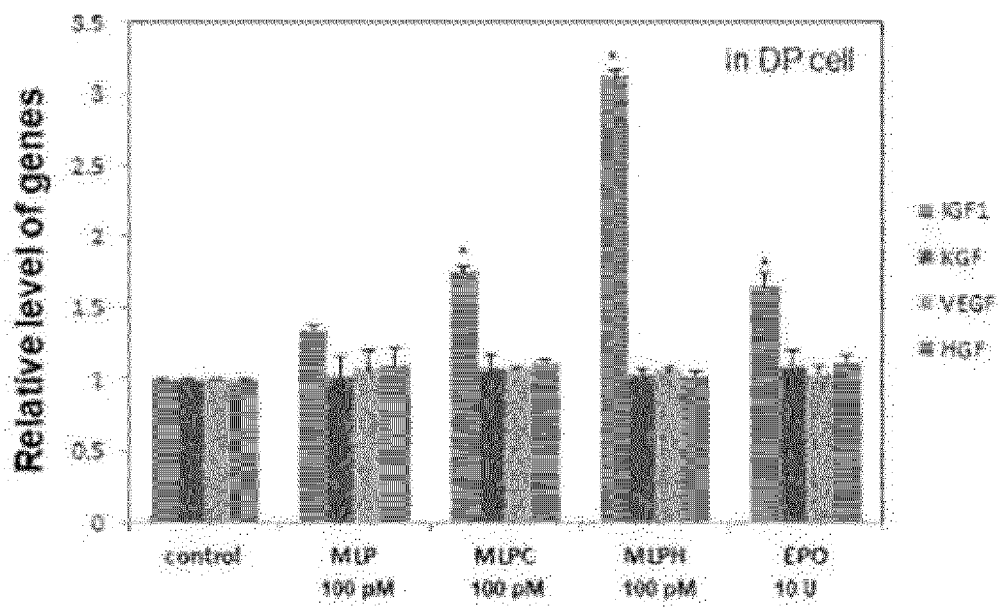

[FIG. 4]
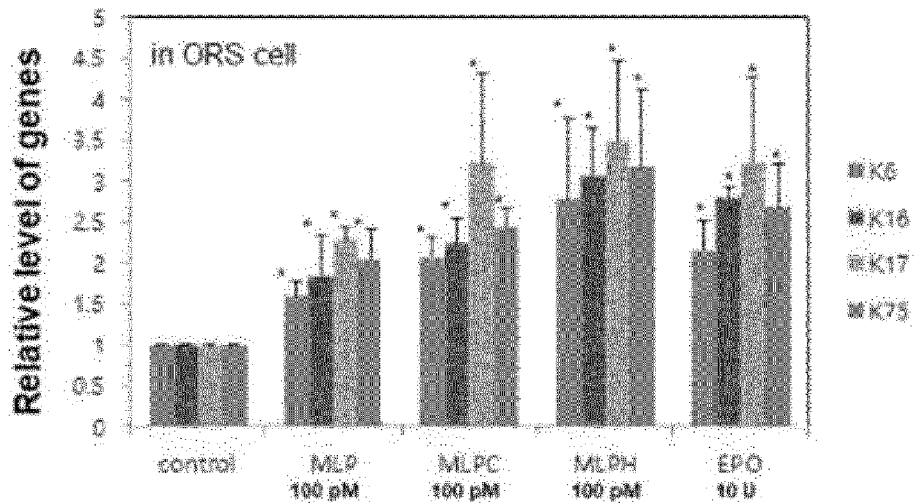
[FIG. 5]
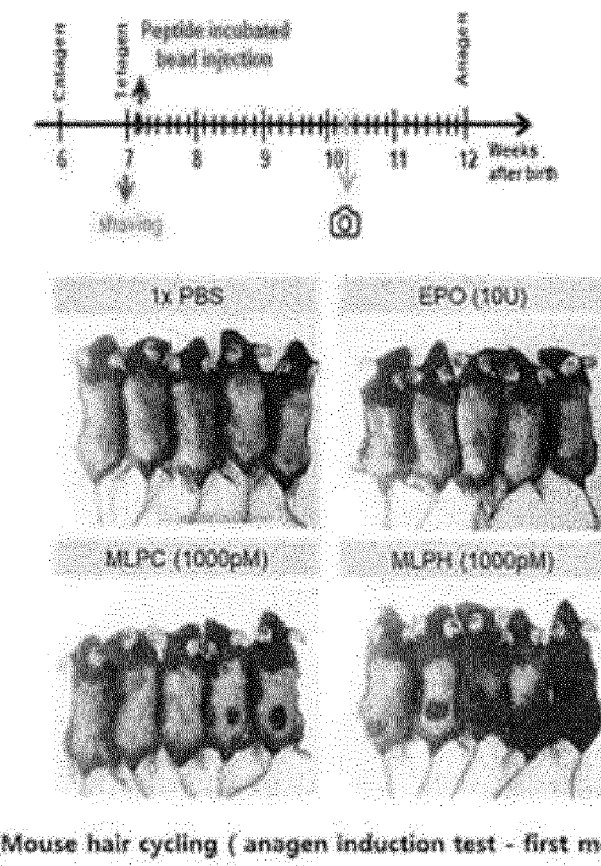
(Mouse hair cycling (anagen induction test - first model))

[FIG. 6]
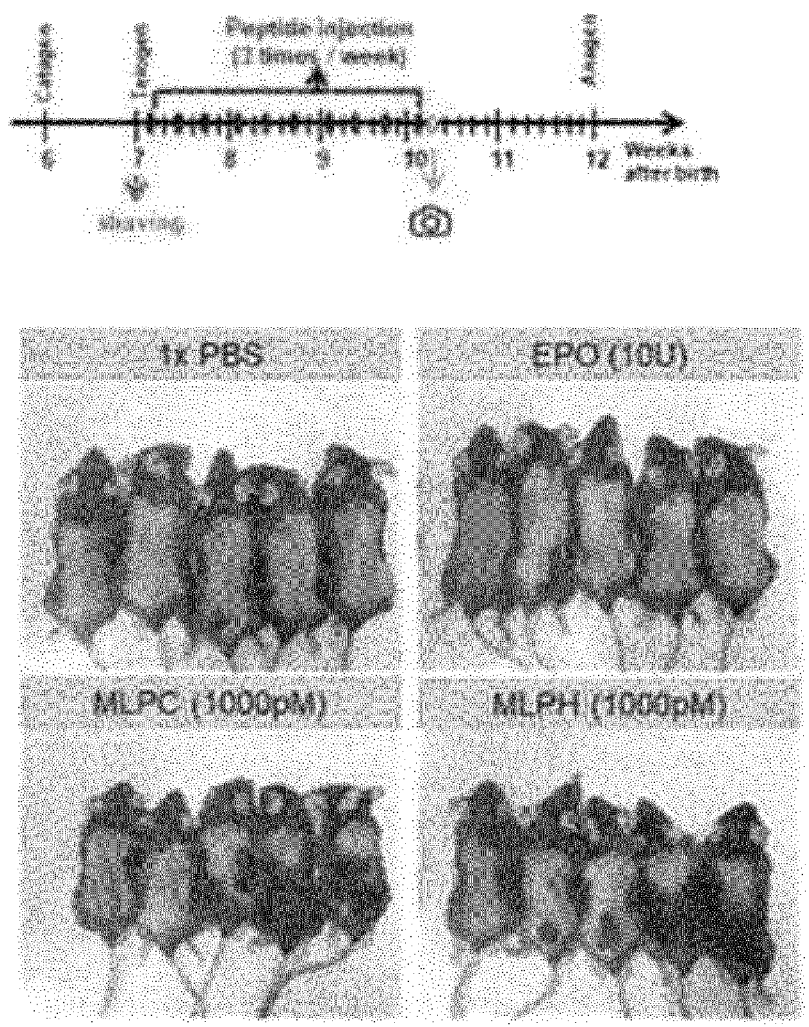

[FIG. 7]
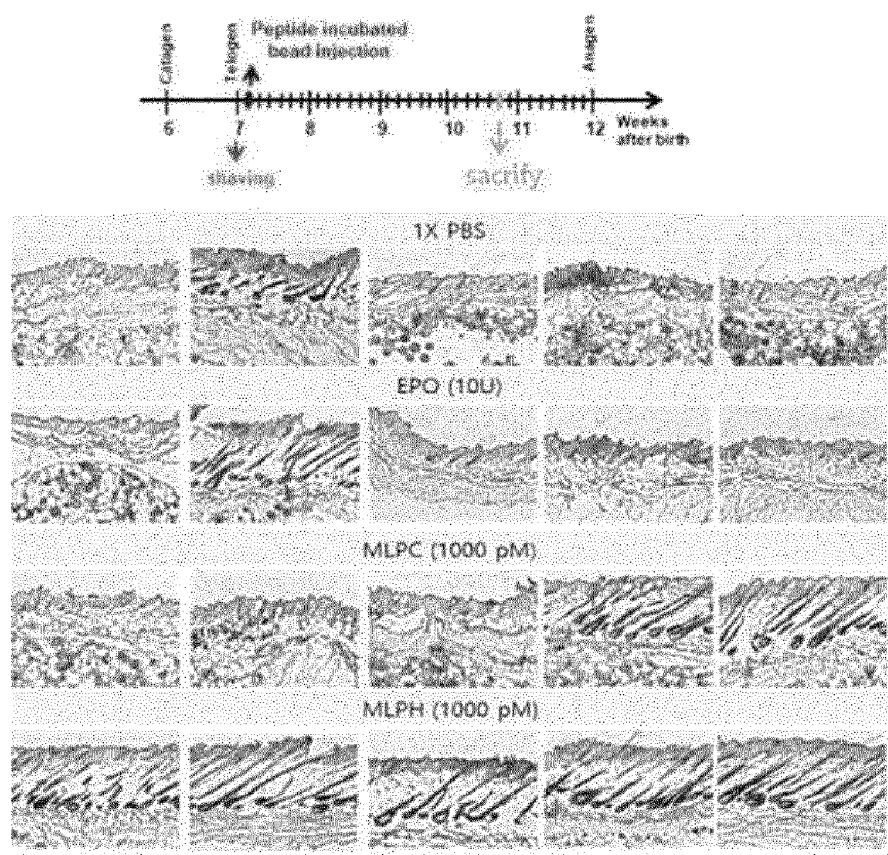

[FIG. 8]
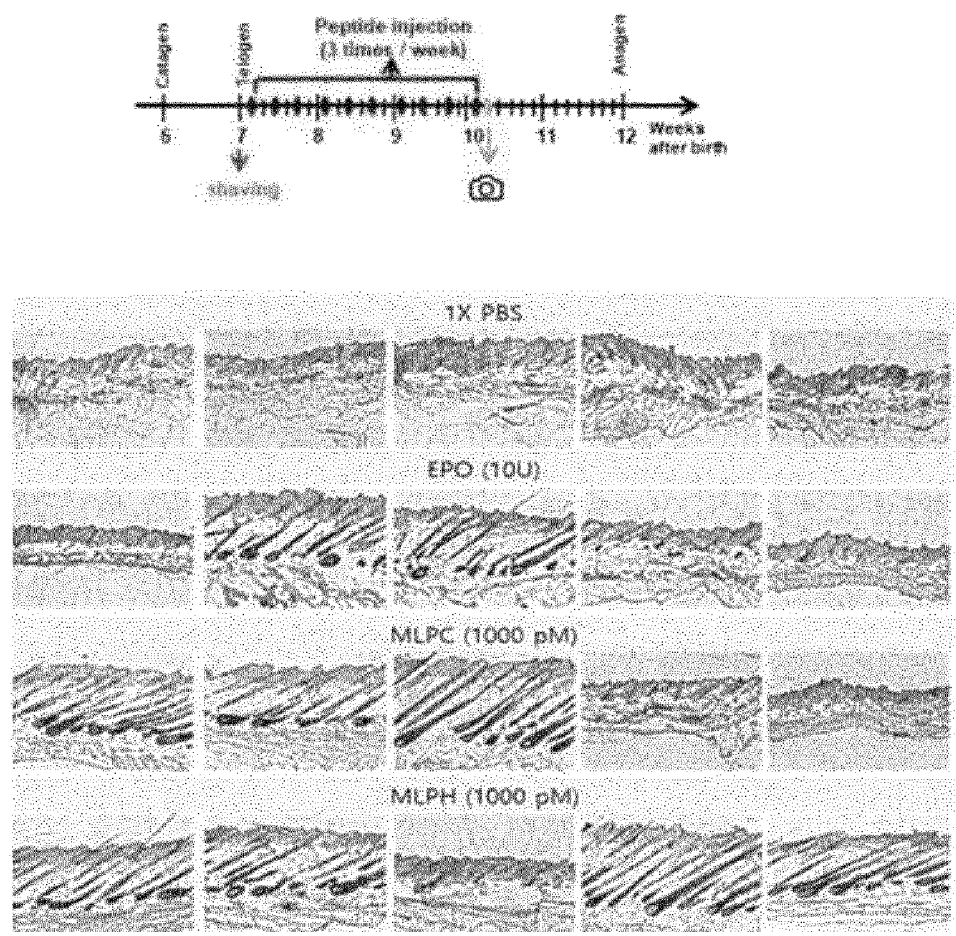

PEPTIDE FOR PREVENTING OR TREATING HAIR LOSS, AND USE THEREOF

TECHNICAL FIELD

The present disclosure relates to a peptide for preventing or treating hair loss, and a use thereof.

BACKGROUND ART

Testosterone is involved in skeletal muscle increase, genital development, spermatogenesis, and sexual desire, which are normal aspects of physical characteristics in men. On the other hand, the negative aspects such as acne, sebum increase, hair loss, and prostatic hypertrophy are developed as dihydrotestosterone acts on related tissues. Thereamong, research on hair loss, which is dominant in men, has been conducted for a long time, but the mechanism of hair loss and hair growth has not been accurately elucidated. However, in a modern society that values appearance, the need for prevention and treatment thereof is becoming urgent.

Recently, cases of hair loss in women are also increasing. Although an increase in androgens is not observed in most patients with female pattern baldness, a thyroid disease as well as a lack of iron and trace elements in the body are known to be the causes. Although female pattern baldness is largely affected by the maternal line (mother side), the family history is not clear, compared to male pattern baldness. Recently, as the number of female pattern baldness is increasing, the demand for various types of treatments and procedures is rising in the beauty industries and the related fields.

Hair is a living organism that regularly repeats the cyclical changes including an anagen phase, a catagen phase, and a telogen phase. In addition, each hair repeats independent generation and destruction, thereby maintaining a constant number of hairs. The number of hairs is determined from birth. However, after puberty, a process of turning into terminal hair due to effects of sex hormones is often mistaken as an increase in the number. The anagen phase is a period in which hair grows due to the activity of hair follicles and active cell division and is maintained for about 2-6 years. About 85% of all hair is in this phase. Hair bulb cells in the anagen phase are surrounded by hair papilla consisting of stromal cells to have a circular shape, and cell division for the production of new hair is active. The catagen phase is a period in which hair follicles stop growing and shrink rapidly. At this time, the shape of hair is similar to a club. It takes about 2-3 weeks, and about 5% of the entire hair is in the catagen phase. The telogen phase is a period in which the cell activity of hair follicles completely disappears. During the period of 2-3 months, the hair follicles are pushed and fall out by hair in the anagen phase that grows from the base of the hair in the telogen phase, or naturally fall out by mechanical action such as combing or hair washing. In general, alopecia refers to an increase in the number of hairs that are abnormally fallen out due to reduction in the proportion of hair in the anagen phase while the number of hair in the catagen phase or the telogen phase increases during the growth cycle.

The causes of alopecia with hair fallen out from the scalp are diverse, and are broadly divided into action of male hormone, mental stress, lipid peroxide accumulation in the scalp, drug side effects, chronic diseases such as leukemia or tuberculosis, side effects caused by radiation therapy, and nutrition deficiency. In addition, hair loss has been known to be a problem for men in recent years. However, a demand for prevention and treatment for female hair loss and specifically hair loss among young people is growing.

Drugs currently used as hair growth and hair tonic agents include vasodilators to circulate sufficient blood to the scalp, female hormones to inhibit the action of male hormones, and anti-androgen to inhibit 5α-reductase which converts testosterone to 5-dihydrotestosterone (5-DHT). The vasodilators include carpronium chloride, minoxidil, and various plant extracts, the female hormones include estrogen, estradiol, and progesterone, and the anti-androgen includes finasteride and pentadecanoic acid.

However, due to insufficient effects or side effects of the hair loss treatment, development of more effective and safe treatment for hair loss or hair tonic is required. Minoxidil which is administered topically or orally brings irritation to the skin such as erythema, inflammation, infection, irritation, or pain on the scalp, and has an effect of lowering blood pressure. Thus, hypertensive patients, including those taking antihypertensive drugs, should take caution in the administration. Moreover, finasteride has disadvantages such as erectile dysfunction and reduction in sexual desire due to an effect of inhibiting male hormone activity.

Accordingly, the present inventors have solved the above issues by inventing an erythropoietin-derived peptide to lower the risk of side effects, unlike the existing chemical-based compositions.

DISCLOSURE

Technical Goals

Example embodiments of the present disclosure provide a pharmaceutical composition for preventing and treating hair loss or promoting hair growth, including a peptide including any one amino acid sequence selected from the group consisting of SEQ ID NOs: 1 to 3 as an active ingredient.

In addition, example embodiments of the present disclosure provide a skin external preparation composition for preventing or ameliorating hair loss, including a peptide including any one amino acid sequence selected from the group consisting of SEQ ID NOs: 1 to 3.

Advantageous Effects

A composition according to one aspect includes a novel peptide. According to a peptide, a pharmaceutical composition including the same, and a skin external preparation according to one aspect, the growth of individual hair follicle cells is promoted, and cytokines for hair expression are increased to have hair tonic, hair growth, or hair growth-promoting effect, thereby securing an effect of treating, ameliorating, or preventing alopecia effectively.

BRIEF DESCRIPTIONS OF THE DRAWINGS

FIG. 1 shows graphs of an analysis conducted by MTT assay 3 days after treating dermal papilla cells with three types of peptides according to one aspect.

FIG. 2 shows a graph of the length measurement 3, 6, and 9 days after treating human hair follicle organ culture with three types of peptides according to one aspect.

FIG. 3 shows a graph of identifying an amount of gene expression of important cytokines involved in the proliferation of hair growth-related cells by treating dermal papilla cells with three types of peptides according to one aspect.

FIG. 4 shows a graph of identifying an amount of gene expression of important cytokine involved in the proliferation of hair growth-related cells by treating outer root sheath cells with three types of peptides according to one aspect.

FIG. 5 shows images of checking the length growth of hair by injecting three types of peptides according to one aspect into the skin of an animal.

FIG. 6 shows images of checking the length growth of hair by injecting three types of peptides according to one aspect three times into the skin of an animal.

FIG. 7 shows images of identifying the length growth and growth cycle of hair with a microscope by injecting three types of peptides according to one aspect into the skin of an animal.

FIG. 8 shows images of identifying the length growth and growth cycle of hair with a microscope by injecting three types of peptides according to one aspect three times into the skin of an animal.

BEST MODE

One aspect provides a peptide including any one amino acid sequence selected from the group consisting of SEQ ID NOs: 1 to 3. The peptide may be derived from the sequence of an erythropoietin protein. The peptide may bind to an erythropoietin receptor. For example, it may bind to a target site (site 1) or a target site (site 2) of the receptor.

Another aspect provides a pharmaceutical composition for preventing and treating hair loss or promoting hair growth, including a peptide including any one amino acid sequence selected from the group consisting of SEQ ID NOs: 1 to 3 as an active ingredient.

The term "hair loss" as used herein refers to a state in which there is no hair in a region where hair should exist or a state with low hair density or thin, weakened hair. In general, it is considered that there is a high possibility of hair loss if the number of hair lost per day is about 100 or more.

According to an example embodiment, the hair loss may be female pattern baldness or male pattern baldness. In addition, the hair loss may be one or more selected from the group consisting of alopecia areata, hereditary androgenetic alopecia, telogen alopecia, traumatic alopecia, trichotillomania, pressure alopecia, anagen effluvium, alopecia pityroides, syphilitic alopecia, seborrheic alopecia, symptomatic alopecia, scarring alopecia, or congenital alopecia.

The peptide may be derived from the sequence of an erythropoietin protein, and the peptide may be derived from an erythropoietin binding site.

The peptide has a binding affinity of 0.1 µM to 1 nM for the erythropoietin receptor. Specifically, the erythropoietin receptor has two target sites and forms a conjugate with erythropoietin. Of the two binding target sites, it is known that target site 1 forms a strong binding (KD=~1 nM) and target site 2 forms a weak bond (KD=~1 µM). The peptide according to one aspect may regulate the cell proliferation effect by forming a weak bond with the target site 2 in the erythropoietin receptor.

The peptide may form an alpha helix structure and additionally have a cytoprotective activity. In addition, the peptide may promote proliferation or differentiation of hematopoietic stem cells, adipocytes, pancreatic cells, muscle cells, vascular cells, hair follicle cells, or skin cells.

In an example embodiment, the peptide may promote the growth of dermal papilla cells or matrix cells. In addition, the peptide may promote the growth of outer root sheath cells or inner root sheath cells.

In an example embodiment, the peptide may promote the expression of hair growth-related cytokines. Specifically, the peptide may promote the expression of insulin-like growth factor 1 (IGF1) in dermal papilla cells. Since proliferation of the dermal papilla cell refers to proliferation of stem cells that produce hair, there may be an effect of promoting hair growth. Therefore, if the expression of the differentiation marker is stimulated, there may be an effect of promoting hair growth to make the hair grow well.

In addition, in the outer root sheath cells, it may be to promote the expression of K6, K16, K17, or K75, which are markers for keratinocyte differentiation. The differentiation of the outer root sheath cells refers to an effect of promoting hair growth, that is, thickening the hair, thereby securing a favorable hair tonic effect. Therefore, when the expression of the differentiation marker is stimulated, there may be an effect of helping the hair grow well due thickened hair.

In an example embodiment, the peptide may be included in an amount of 10 ppm to 10000 ppm. Specifically, the content may be 20 ppm to 10000 ppm, 10 ppm to 8000 ppm, 30 ppm to 6000 ppm, 50 ppm to 5000 ppm, 70 ppm to 4000 ppm, 80 ppm to 3000 ppm, 100 ppm to 2500 ppm, 110 ppm to 2000 ppm, 150 ppm to 1800 ppm, 200 ppm to 1500 ppm, 300 ppm to 1400 ppm, 400 ppm to 1300 ppm, 500 ppm to 1250 ppm, 600 ppm to 1200 ppm, 700 ppm to 1200 ppm, 800 ppm to 1230 ppm, 900 ppm to 1100 ppm, or 750 ppm to 1150 ppm. Preferably, 1000 ppm may be included. The best effect of ameliorating and treating hair loss or promoting hair growth may be derived when the peptide is present in the content listed above.

According to an example embodiment, the peptide may have a hair growth, hair growth-promoting, or hair tonic effect.

The term "hair growth" as used herein refers to a phenomenon that hair grows. That is, it broadly includes growth of new hair. The term "hair tonic" or "hair growth-promotion" as used herein refers to an action of making hair grow long. That is, hair tonic or hair growth-promotion refers to an action of broadly increasing the root, circumference, length, and strength of hair by thickening and strengthening the hair.

According to an example embodiment, the peptide may have all the hair tonic or hair growth-promoting and hair growth effects. Therefore, according to the composition in one aspect, there may be an effect of newly growing hair as well as an effect of increasing the thickness of existing hair and strengthening entire hair.

The term "prevention" as used herein refers to any action that inhibits hair loss or delays the onset thereof via administration of the pharmaceutical composition according to one aspect.

The term "amelioration" refers to any action that reduces a parameter related to an abnormal state of hair loss, for example, the degree of a symptom at least by administration of the pharmaceutical composition according to one aspect.

The term "treatment" as used herein refers to any action that a disease or symptom of hair loss is alleviated or beneficially changed by the administration of the pharmaceutical composition according to one aspect. In this case, the composition may be used simultaneously with or separately from a drug for treatment before or after the onset of the disease in order to prevent or ameliorate hair loss.

Also, the term "active ingredient" or "pharmaceutically effective amount" as used herein refers to any amount of a composition used in the practice of the disclosure provided herein, sufficient to alleviate, inhibit the progression, or prevent a disease, disorder or condition, or one or more symptoms thereof.

The terms "administering," "introducing," and "implanting" as used herein are used interchangeably and may refer to placement of a composition according to an example embodiment into a subject by a method or route that leads to at least partial localization of the composition according to an example embodiment to a desired site. The composition according to one aspect may be administered by any suitable route to deliver the composition to a desired site in a living individual.

The term "pharmaceutically acceptable" as used herein refers to a composition suitable for use in contact with the tissues of a subject (e.g., a human) within the scope of appropriate medical judgment owing to the reasonable benefit/risk ratio without excessive toxicity, irritation, allergic reaction, or other problems or complications.

The pharmaceutical composition may include a pharmaceutically acceptable carrier in addition to the active ingredient. In this case, the pharmaceutically acceptable carriers are those commonly used in formulation, including lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, but are not limited thereto. In addition, a lubricant, a wetting agent, a sweetening agent, a flavoring agent, an emulsifying agent, a suspending agent, and a preservative may be additionally included in addition to the above components.

The pharmaceutical composition may be administered orally (oral preparation) or parenterally (e.g., as an inhalant or injection applied intravenously, subcutaneously, intraperitoneally, or topically) according to a desired method. For example, it may be administered subcutaneously (i.e., skin external preparation) or orally (i.e., oral preparation), but is not limited thereto.

As a buffer to be added to the above various formulations, it is preferable to use an isotonic, non-irritating solution in pH 4-9 and pH 5-9. The dosage varies depending on the condition and weight of a patient, the degree of disease, the drug type, the administration route, and duration, but may be appropriately selected by those skilled in the art.

According to an example embodiment, the peptide or pharmaceutical composition may be injected by a method of directly injecting under the skin of an individual or a method of injecting the peptide or pharmaceutical composition into a bead which is then injected into the body. The subcutaneous injection method may be an injection type using a syringe or a patch injection type using a nanoneedle. The patch injection type may be free from inconvenience that occurs in the direct injection type requiring frequent injections.

The pharmaceutical composition may be administered in a pharmaceutically effective amount. The term "pharmaceutically effective amount" as used herein refers to an amount sufficient to treat a disease with a reasonable benefit/risk ratio applicable to medical treatment. The effective dose level may be determined by the disease type of a patient, severity, activity of a drug, sensitivity to the drug, administration time, administration route and excretion rate, duration of treatment, factors including drug used in combination with, and other factors well known in the medical field. Other pharmaceutical compositions of an example embodiment of the present disclosure may be administered as individual therapeutic agents or in combination with other therapeutic agents, and also administered sequentially or simultaneously with conventional therapeutic agents. In addition, single or multiple administration may be allowed. Taking all the factors above into consideration, it is important to administer an amount capable of obtaining the best effect with a minimum amount without side effects, which may be easily determined by those skilled in the art.

The effective amount of the pharmaceutical composition may vary depending on the patient's age, sex, condition, body weight, absorption rate of the active ingredient into the body, inactivation rate and excretion rate, disease type, and drugs used in combination, and may be generally in the range of 0.1 to 500 mg per 1 kg a day. Administration may be conducted daily or every other day, in divided doses within the range of 1 to 5 times a day. However, since it may be increased or decreased depending on the route of administration, severity of obesity, sex, body weight, and age, the dosage does not limit the range in any way.

Another aspect provides a method for preventing or treating hair loss, including administering a pharmaceutically effective amount of the composition to an individual who is in need thereof, coming into contact with cells in vitro, or administering to an experimental animal in vivo. Specific details on the peptide and hair loss are the same as described above.

The composition according to an example embodiment may include any one or more peptides selected from the group consisting of SEQ ID NOs: 1 to 3 in an amount of 0.001 wt % to 80 wt % with respect to the total weight of the composition.

In an example embodiment, the peptide may be contained in an amount of 10 ppm to 10000 ppm. Specifically, the content may be 20 ppm to 10000 ppm, 10 ppm to 8000 ppm, 30 ppm to 6000 ppm, 50 ppm to 5000 ppm, 70 ppm to 4000 ppm, 80 ppm to 3000 ppm, 100 ppm to 2500 ppm, 110 ppm to 2000 ppm, 150 ppm to 1800 ppm, 200 ppm to 1500 ppm, 300 ppm to 1400 ppm, 400 ppm to 1300 ppm, 500 ppm to 1250 ppm, 600 ppm to 1200 ppm, 700 ppm to 1200 ppm, 800 ppm to 1230 ppm, 900 ppm to 1100 ppm, or 750 ppm to 1150 ppm. Preferably, the content may be about 1000 ppm. The most outstanding effects of ameliorating and treating hair loss or promoting hair growth may be derived if the peptide is present in an amount listed above. In addition, the peptide or composition may be administered 1 to 6 times a day. Specifically, the number of administration may be one time or two or more times within the range of clinically acceptable side effects. Regarding the administration site, the administration may be performed in one site or two or more sites. Preferably, it may be administered 1 to 3 times.

In addition, the dosage of the composition may be 0.01 mg to 10,000 mg, 0.1 mg to 1000 mg, 1 mg to 100 mg, 0.01 mg to 1000 mg, 0.01 mg to 100 mg, 0.01 mg to 10 mg, or 0.01 mg to 1 mg. However, the dosage may be prescribed in various ways depending on factors such as formulation method, administration type, patient's age, weight, sex, pathological condition, food, administration time, administration route, excretion rate, and reaction sensitivity, and those skilled in the art may appropriately adjust the dosage in consideration of these factors. For animals other than humans, the same dosage may be applied as that of humans per kg or, for example, an amount obtained by converting the above dosage by the volume ratio (e.g., average value) of the target animal and the organ (e.g., heart) of the human.

Possible routes of administration may include oral, sublingual, parenteral (e.g., subcutaneous, intramuscular, intraarterial, intraperitoneal, intrathecal, or intravenous), rectal, topical (including transdermal), inhalation, and injection or implantable devices or the insertion of a substance.

According to an example embodiment, the peptide or the pharmaceutical composition may be injected by a method of directly injecting under the skin of an individual or injecting the peptide or the pharmaceutical composition into a bead which is then injected into the body. The subcutaneous injection method may be a patch injection type using a nanoneedle. The patch injection type may be free from inconvenience that occurs in the direct injection type requiring frequent injections.

The subject according to an example embodiment includes humans and other targets such as mammals, and specifically includes humans, monkeys, mice, rats, rabbits, sheep, cattle, dogs, horses, and pigs.

The pharmaceutical composition according to an example embodiment may include a pharmaceutically acceptable carrier and/or additive. For example, sterile water, physiological saline, conventional buffers (phosphoric acid, citric acid, and other organic acids), stabilizers, salts, antioxidants (ascorbic acid), surfactants, suspending agents, isotonic agents, or preservatives. For topical administration, also included is a combination with organic materials such as biopolymers and inorganic materials such as hydroxyapatite, specifically collagen matrix, polylactic acid polymers or copolymers, polyethylene glycol polymers or copolymers, and chemical derivatives thereof. In the case that the pharmaceutical composition according to an example embodiment is prepared in a form suitable for injection, the peptide may be dissolved in the pharmaceutically acceptable carrier or frozen in a dissolved solution.

The pharmaceutical composition according to an example embodiment may appropriately include, if needed depending on the administration type or formulation, suspending agents, solubilizing adjuvants, stabilizers, isotonic agents, preservatives, adsorption inhibitors, surfactants, diluents, excipients, pH adjusters, analgesic agents, buffers, reducing agents, and antioxidants. The pharmaceutically acceptable carriers and formulations suitable for the present disclosure, including those exemplified above, are described in detail in the reference [Remington's Pharmaceutical Sciences, 19th ed., 1995]. The pharmaceutical composition according to an example embodiment may be formulated in a unit dosage form by using the pharmaceutically acceptable carrier and/or excipient according to a method that may be easily carried out by a person of ordinary skill in the art to which the present disclosure pertains, or prepared by putting the same in a multi-dose container. In this case, the formulation may be in the form of a solution, a suspension, or an emulsion in an oil or aqueous medium or in the form of powder, granules, tablets, or capsules.

Another aspect provides a functional health food composition for preventing or ameliorating hair loss, including a peptide consisting of any one amino acid sequence selected from the group consisting of SEQ ID NOs: 1 to 3 as an active ingredient.

Specific details on the peptide and hair loss are the same as described above.

For the food composition, there is no specific limitation in components that are added, other than the active ingredient contained as an essential component in the indicated ratio. Various flavoring agents or natural carbohydrates may be included as additional ingredients like a conventional beverage. Examples of the above-mentioned natural carbohydrates include monosaccharides such as glucose and fructose; disaccharides such as maltose and sucrose; and polysaccharides such as conventional sugars including dextrin and cyclodextrin, and sugar alcohols such as xylitol, sorbitol, and erythritol. As flavoring agents other than those described above, natural flavoring agents (thaumatin, a stevia extract such as rebaudioside A and glycyrrhizin) and synthetic flavoring agents (saccharin, aspartame) may be advantageously applied. The ratio of the natural carbohydrate may be appropriately determined by the selection of those skilled in the art.

In addition to the above, the food composition may include various nutrients, vitamins, minerals (electrolytes), flavoring agents such as synthetic flavoring agents and natural flavoring agents, coloring agents and thickening agents (cheese, chocolate), pectic acid and salts thereof, alginic acid and salts thereof, organic acids, protective colloidal thickeners, pH adjusters, stabilizers, preservatives, glycerin, alcohols, and carbonating agents used in carbonated beverages. These components may be used independently or in combination. The proportion of the additives may also be appropriately selected by those skilled in the art.

Another aspect provides a skin external preparation composition for preventing or ameliorating hair loss, including a peptide including any one amino acid sequence selected from the group consisting of SEQ ID NOs: 1 to 3.

Specific details on the peptide and hair loss are the same as described above.

The composition has hair growth-promoting, hair tonic, or hair growth effects. Therefore, it is possible to prevent or ameliorate hair loss by promoting growth of hair to make hair grow, increase the activity of hair-related keratin and cytokines in the body, and increase the expression of hair-related cells, thereby enhancing the overall hair growth activity of an individual.

According to an example embodiment, the prevention or amelioration of hair loss may include promoting hair growth or increasing hair thickness.

According to an example embodiment, the hair loss may be female pattern baldness or male pattern baldness. In addition, the hair loss may be one or more selected from the group consisting of alopecia areata, hereditary androgenetic alopecia, telogen alopecia, traumatic alopecia, trichotillomania, pressure alopecia, anagen effluvium, alopecia pityroides, syphilitic alopecia, seborrheic alopecia, symptomatic alopecia, scarring alopecia, or congenital alopecia.

The skin external preparation composition refers to a composition of all formulations that may be applied on the skin surface except for quasi-drugs. According to an example embodiment, the skin external preparation composition may be a quasi-drug or a cosmetic composition.

According to an example embodiment, the skin external preparation may be one or more selected from the group consisting of hair growth agents, scalp clinic agents, scalp scaling agents, scalp massage agents, scalp care agents, cleansers, shampoos, tonics, hair conditioners, hair lotions, gels, packs, creams, essences, powder, sprays, oil, soaps, ointments, hair styling agents, hair dyes, perm, scalp tonics, scalp lotions, scalp creams, scalp serums, hair mousses, hair gels, eyebrow growth promoting agents, eyelash growth promoting agents, eyelash nutrition agents, and pet shampoos, or pet conditioners.

The term "quasi-drug" as used herein refers to a composition having a lower pharmaceutical action than a therapeutic composition or a pharmaceutical composition. The term "cosmetic composition" as used herein refers to a composition used in the human body to clean and care the human body to add more charms, to brighten the appearance, or to maintain or promote condition of skin and hair.

For example, if the peptide of one aspect is included in a high amount, it may be classified as a therapeutic composition, and if there is a pharmaceutical action but it is lower than the therapeutic composition, it may be classified as a quasi-drug for skin. It may be classified as a cosmetic composition if the pharmaceutical action is mild and it is intended to be applied for skin care. Accordingly, the quasi-drug for skin and cosmetic composition as described above may be collectively referred to as a skin external preparation composition.

According to an example embodiment, a hair growth promoting agent, a scalp care agent, a gel, a pack, a cream, an essence, powder, a spray, oil, soap, or an ointment containing the peptide of one aspect as an active ingredient may be a quasi-drug for skin external preparation.

According to another example embodiment, a scalp clinic agent, a scalp scaling agent, a scalp massage agent, a scalp care agent, a cleanser, a shampoo, a tonic, a hair conditioner, a hair lotion, a gel, a pack, a cream, an essence, powder, spray, oil, soap, ointment, hair styling agent, a hair dye, a perm, a scalp tonic, a scalp lotion, a scalp cream, a scalp serum, a hair mousse, a hair gel, an eyebrow growth promoting agent, eyelash growth promoting agent, eyelash nutrition agent, or a pet shampoo or a pet conditioner containing the peptide of one aspect may be a cosmetic composition.

When the peptide is added to the quasi-drug composition for the purpose of preventing or ameliorating hair loss, the peptide including the sequence number may be added as it is or used in combination with other quasi-drug components, and may be used appropriately according to a conventional method. The mixing amount of the active ingredient may be appropriately determined depending on the purpose of use (prophylactic, health care, or therapeutic treatment).

According to an example embodiment, the peptide may be contained in an amount of 10 ppm to 10000 ppm. Specifically, the content may be 20 ppm to 10000 ppm, 10 ppm to 8000 ppm, 30 ppm to 6000 ppm, 50 ppm to 5000 ppm, 70 ppm to 4000 ppm, 80 ppm to 3000 ppm, 100 ppm to 2500 ppm, 110 ppm to 2000 ppm, 150 ppm to 1800 ppm, 200 ppm to 1500 ppm, 300 ppm to 1400 ppm, 400 ppm to 1300 ppm, 500 ppm to 1250 ppm, 600 ppm to 1200 ppm, 700 ppm to 1200 ppm, 800 ppm to 1230 ppm, 900 ppm to 1100 ppm, or 750 ppm to 1150 ppm. Preferably, the content may be about 1000 ppm. The most outstanding effects of ameliorating and treating hair loss or promoting hair growth may be derived if the peptide is present in an amount listed above.

MODES FOR CARRYING OUT INVENTION

Hereinafter, preferred examples will be presented to help the understanding of the present disclosure. However, the following examples are merely provided for easier understanding of the present disclosure, and the contents of the present disclosure are not limited by the following examples.

EXAMPLE

Example 1. Synthesis of Peptides for Hair Loss Treatment

An erythropoietin-derived peptide according to one aspect was synthesized in a form of monomer according to a conventionally known solid phase peptide synthesis technique (Peptron, Daejeon, Korea). Specifically, an erythropoietin-derived peptide capable of binding to an important amino acid sequence (Arg103, Ser104, Leu105, Leu108, and Arg110) among the sequences of the target site (site 2) of a natural erythropoietin receptor was synthesized, and liquid chromatography/mass selective detector (HP1100 series) was used for the measurement of the concentration of the synthesized peptide. The measurement of purity was conducted via high performance liquid chromatography (SHIMADZU prominence HPLC) analysis (>95% purity).

Example 2. Method of Preparing a Hair Cell Model 2.1 Isolation of Hair Follicles in the Anagen Phase In order to test an effect of the peptide of Example 1 on hair, the present inventors prepared a hair cell model. Specifically, scalp tissues of a healthy, normal adult were obtained from a hair transplant patient to isolate hair follicles in the anagen phase.

Specifically, a hair follicle cell isolation medium was prepared to isolate dermal papilla cells and outer root sheath cells from hair follicles in the anagen phase. The hair follicle cell isolation medium was prepared by adding 20% FBS (Hyclone) to a basal medium containing DMEM/low glucose (Hyclone).

As a result, it was possible to isolate hair follicles in the anagen phase from adult scalp tissues.

2.2 Isolation of Hair Follicle Constituting Cells from the Isolated Hair Follicle Organs Using hair follicle cells isolated in Example 2.1, dermal papilla cells and outer root sheath cells, which are hair follicle organs, were isolated. Specifically, the hair follicle cells in the anagen phase were cultured using a follicle organ culture medium.

The culture of the hair follicle cells in the anagen phase was performed in an incubator at 37° C. under condition satisfying 5% CO2/95% air after adding 1000 μl of the hair follicle organ culture medium. The medium was replaced once every 4 days of culture, and the second passage was mainly used for the experiment.

Specifically, William E medium (Gibco) was used as a basic medium for the hair follicle organ culture medium with addition of 100 u/ml of penicillin/streptomycin, 2 mM L-glutamin, 10 ug/ml of insulin, and 10 ng/ml of hydrocortisone.

As a result, it was possible to isolate the dermal papilla cells and outer root sheath cells, which are hair follicle organs, from the hair follicle cells in the anagen phase.

2.3 Culture of Hair Follicle Constituting Cells

In order to prepare a cell model for testing the effect of the peptide for hair loss treatment, the hair follicle organ isolated in Example 2.2 was cultured.

Specifically, two hair follicles per well were placed in the hair follicle organ culture medium, and cultured at 37° C. under condition satisfying 5% CO2/95% air. The medium was replaced once every 3 days.

For the follicle organ culture medium, each different medium was used for follicle organs. Outer root sheath cells were cultured in EpiLife medium (Cascade Biologics), and dermal papilla cells were cultured in DMEM (Hyclone)-based basal medium added with penicillin (100 U/ml), streptomycin (100 ug/ml), and 20% FBS. The EpiLife medium is a sterile liquid medium containing 60 μM calcium chloride.

As a result, 15 isolated dermal papilla cells (DP cell isolation) and 30 outer root sheath cells (ORS cell isolation) were harvested.

The dermal papilla cells (DP cells), a group of skin mesenchymal cells, not only regulate the development and growth of hair follicles, but are also known as a reservoir of pluripotent stem cells, and thus are important for hair loss treatment.

In addition, the outer root sheath cell (ORS cell) is a cell surrounding the fibers of hair and the inner root sheath. The outer root sheath cells are composed of basal cells on the surface of the skin, prickle cells, and granular layers. It may also include cells performing specific functions of hair follicles, representing an alternative source of keratinocytes suitable for skin replacement.

EXPERIMENTAL EXAMPLE

Experimental Example 1. Identification of an Effect of Peptides for Hair Loss Treatment in Cell Experiments 1.1 Peptide Treatment by Concentration in Hair Follicle Organs Using the peptide of Example 1, the effect of treating or preventing hair loss in the cell model in Example 2 was identified. The cell model was treated with the peptide of each different concentration of 1 pM, 100 pM, and 1000 pM, respectively. Scr peptide was treated as a negative control group. The purity of all peptides used in the experiment was 95% or higher.

1.2 Cell Viability Measurement Using MTT Assay

The dermal papilla cells and outer root sheath cells in Example 2 were cultured in a 96 well plate respectively, and then the peptides were treated in serum free media by type and concentration. Next, after 3 days, the cells were measured at 570 nm after treatment of MTT solution. At the same time, the non-treated negative control group and a control group treated with 10 U of erythropoietin were also compared by performing MTT analysis.

10 U has a binding degree similar to EPOR as compared to 1000 pM peptide.

1.3 Cell Viability Measurement Using Real-Time PCR

In order to detect the genes expression level of cytokine crucial for dermal papilla cell proliferation, the dermal papilla cells and outer root sheath cells in Example 2 were treated with each peptide, followed by total RNA isolation after 24 hours. Next, cDNA was synthesized from the isolated total RNA, and the synthesized cDNA was subjected to PCR using a primer of a gene to be analyzed.

1.4 Identification of Growth of Hair Follicles Over Incubation Time

The human hair follicle cells in Example 2 were treated with the peptide of the present disclosure by concentration, followed by culture for 3, 6, and 9 days. After culture, pictures of the grown hair follicle cells were taken for comparison using a microscope. The length of the grown hair was measured and expressed in mm At the same time, the length of grown hair was measured and compared in the non-treated negative control group and the control group treated with 10 U of erythropoietin. 10 U has a binding degree similar to EPOR as compared to 1000 pM peptide.

1.5 Identification of an Effect of Peptides in Cell Models

As a result, as shown in FIG. 1, all the peptides of SEQ ID NOs: 1 to 3 showed a high degree of cell differentiation as compared to the negative control group. Moreover, compared with the control group treated with erythropoietin, it was found that the three types of peptides of the present disclosure showed excellent effects even when treated with an amount which causes less binding to the receptor. In this case, since 10 U has the binding degree similar to EPOR as compared to 1000 pM peptide with no specific side effect as erythropoietin is not used, the peptide of one aspect may exhibit hair loss treatment effects in a smaller amount than erythropoietin.

In addition, as shown in FIG. 2, when all the peptides of SEQ ID NOs: 1 to 3 were compared with the negative control group, hair growth was promoted. In addition, compared with the control group treated with erythropoietin, there was no specific side effect since erythropoietin was not used. At the same time, the hair loss treatment effect was derived with a smaller amount than erythropoietin.

Next, as a result of identifying the gene expression level of cytokine important for dermal papilla cell proliferation as shown in FIG. 3, the peptides of SEQ ID NOs: 1 to 3 increased the gene expression level of hair growth-related factors, keratinocytes, and cytokines.

In addition, as a result of identifying the gene expression level of the cytokine important for the differentiation of outer root sheath cells as shown in FIG. 4, it was found that all the cytokines involved in the differentiation of outer root sheath cells were increased. The result showed an effect of thickening the hair, thereby having a favorable effect on the hair growth.

In particular, compared to the control group treated with erythropoietin, there was no specific side effect since erythropoietin was not used, and at the same time, the degree of increase in the expression was superior even with a smaller amount than erythropoietin.

Since dermal papilla cell proliferation means the proliferation of stem cells that eventually produce hair, it suggests that the hair growth effect is outstanding, and the experimental results indicate that IGF is a cytokine involved in proliferation. It was identified that the effect was more remarkable than that of EPO.

Experimental Example 2. Identification of an Effect of Peptides for Hair Loss Treatment in Animal Experiments 2.1 Peptide Treatment by Concentration in Experimental Animals Using the peptide in Example 1, the effect of treating or preventing hair loss was identified in experimental animals. Specifically, in order to increase the accuracy in the animal experiments, animal experiments were conducted using two methods conducted by injecting a bead subcutaneously into an experimental animal after injecting a peptide into the bead, and by repeatedly injecting the peptide. Experimental animals were divided into an experimental group of bead-peptide injection models and an experimental group of peptide injection models depending on the injection method. The experimental animals in both experimental groups were treated with 1000 pM peptide, respectively.

Bio-rad Bead products (#153-7302) were used for the experimental group of bead-peptide injection models. Specifically, impurities on the beads were removed and washed, and then each peptide and beads were combined and incubated at 37° C. Next, the finally bound bead-peptides were injected into the subcutaneous fat layer of the experimental animal using a needle. In addition, for the experimental group of peptide injection models, the peptide in Example 1 was injected into the subcutaneous fat layer of the experimental animal using injection.

2.2 H and E Staining Analysis Method

After completing the animal experiment, the skin tissue was cut out around the area where the peptide was injected. Tissues were fixed in a fixative and stored frozen after processing the same in a form of frozen sections. Hematoxylin and eosin staining was conducted by cutting the frozen tissue into pieces in the thickness of 10 μm using a sectioning machine.

2.3 Identification of an Effect of Peptides in Experimental Animals

As a result, as shown in FIGS. 5 to 6, it was found that the peptide of one aspect in both methods effectively caused hair to grow.

In particular, as shown in FIGS. 7 and 8, it was observed that MLPH had a superior effect than any other peptide. When the peptide according to one aspect was injected into the experimental animal, an effective hair growth promoting effect was observed in both the bead injection and the peptide injection methods. In particular, in the case of animal experiments, it was found that the peptide of one aspect had a more significant hair growth effect than erythropoietin.

The above results suggest that the peptide of one aspect may effectively function as a composition for hair loss treatment.

What is claimed is:

1. A method of treating hair loss or promoting hair growth, comprising administering to a subject a therapeutically effective amount of a pharmaceutical composition comprising a peptide consisting of SEQ ID NO: 2 or SEQ ID NO: 3 as an active ingredient.

2. The method of claim 1, wherein the peptide promotes growth of dermal papilla (DP) cells or matrix cells.

3. The method of claim 1, wherein the peptide promotes growth of outer root sheath (ORS) cells.

4. The method of claim 1, wherein the peptide promotes expression of hair growth-related cytokines.

5. The method of claim 1, wherein the peptide is contained in an amount of 10 ppm (parts per million) to 10000 ppm.

6. The method of claim 1, wherein the peptide has hair growth effects.

7. The method of claim 1, wherein the hair loss is one or more selected from the group consisting of alopecia areata, hereditary androgenetic alopecia, telogen alopecia, traumatic alopecia, trichotillomania, pressure alopecia, anagen effluvium, alopecia pityroides, syphilitic alopecia, seborrheic alopecia, symptomatic alopecia, scarring alopecia, and congenital alopecia.

8. A method of ameliorating hair loss, comprising administering to a subject a therapeutically effective amount of a skin external preparation composition comprising a peptide consisting of SEQ ID NO: 2 or SEQ ID NO: 3.

9. The method of claim 8, wherein the amelioration of hair loss is to promote hair growth or thicken hair.

10. The method of claim 8, wherein the skin external preparation composition is a cosmetic composition.

11. The method of claim 8, wherein the skin external preparation composition is one or more selected from the group consisting of hair growth agents, scalp clinic agents, scalp scaling agents, scalp massage agents, scalp care agents, cleansers, shampoos, tonics, hair conditioners, hair lotions, gels, packs, creams, essences, powder, sprays, oil, soaps, ointments, hair styling agents, hair dyes, perm, scalp tonics, scalp lotions, scalp creams, scalp serums, hair mousses, hair gels, eyebrow growth promoting agents, eyelash growth promoting agents, eyelash nutrition agents, and pet shampoos, and pet conditioners.

12. The method of claim 8, wherein the peptide is contained in an amount of 10 ppm to 10000 ppm.

13. The method of claim 8, wherein the hair loss is one or more selected from the group consisting of alopecia areata, hereditary androgenetic alopecia, telogen alopecia, traumatic alopecia, trichotillomania, pressure alopecia, anagen effluvium, alopecia pityroides, syphilitic alopecia, seborrheic alopecia, symptomatic alopecia, scarring alopecia, and congenital alopecia.

* * * * *

```
                         SEQUENCE LISTING

<160> NUMBER OF SEQ ID NOS: 4

<210> SEQ ID NO 1
    <211> LENGTH: 19
    <212> TYPE: PRT
    <213> ORGANISM: Artificial Sequence
    <220> FEATURE:
    <223> OTHER INFORMATION: MLP amino acid peptide

<400> SEQUENCE: 1

Leu His Val Asp Lys Ala Val Ser Gly Leu Arg Ser Leu Thr Thr Leu
    1               5                   10                  15

Leu Arg Ala

<210> SEQ ID NO 2
    <211> LENGTH: 19
    <212> TYPE: PRT
    <213> ORGANISM: Artificial Sequence
    <220> FEATURE:
    <223> OTHER INFORMATION: MLP-C amino acid peptide

<400> SEQUENCE: 2

Arg His Val Lys Lys Arg Val Lys Gly Leu Lys Ser Leu Thr Thr Leu
    1               5                   10                  15

Leu Arg Ala

<210> SEQ ID NO 3
    <211> LENGTH: 19
    <212> TYPE: PRT
    <213> ORGANISM: Artificial Sequence
    <220> FEATURE:
    <223> OTHER INFORMATION: MLP-H amino acid peptide

<400> SEQUENCE: 3

Leu His Val Leu Lys Ala Val Ser Gly Leu Leu Thr Leu Thr Met Ile
    1               5                   10                  15

Arg Arg Ala

<210> SEQ ID NO 4
    <211> LENGTH: 19
    <212> TYPE: PRT
    <213> ORGANISM: Artificial Sequence
    <220> FEATURE:
    <223> OTHER INFORMATION: Scr amino acid peptide(negative control)

<400> SEQUENCE: 4

Met Glu Leu Ser Gly Arg Thr Leu Gly Leu Ile Leu Lys Leu Arg Gln
    1               5                   10                  15

Ser Ala Thr
```